(12) United States Patent
Long

(10) Patent No.: US 11,103,263 B2
(45) Date of Patent: Aug. 31, 2021

(54) EMBOLECTOMY SYSTEM AND METHODS OF MAKING AND USING SAME

(71) Applicant: ICHOR Vascular Inc., Eden Prairie, MN (US)

(72) Inventor: Troy Long, Eden Prairie, MN (US)

(73) Assignee: Ichor Vascular Inc., Eden Prairie, MN (US)

( * ) Notice: Subject to any disclaimer, the term of this patent is extended or adjusted under 35 U.S.C. 154(b) by 175 days.

(21) Appl. No.: 15/545,936

(22) PCT Filed: Jul. 23, 2016

(86) PCT No.: PCT/US2016/043769
§ 371 (c)(1),
(2) Date: Jul. 24, 2017

(87) PCT Pub. No.: WO2017/019572
PCT Pub. Date: Feb. 2, 2017

(65) Prior Publication Data
US 2018/0206862 A1 Jul. 26, 2018

Related U.S. Application Data

(60) Provisional application No. 62/196,881, filed on Jul. 24, 2015.

(51) Int. Cl.
*A61B 17/221* (2006.01)
*A61F 2/01* (2006.01)
(Continued)

(52) U.S. Cl.
CPC ...... *A61B 17/221* (2013.01); *A61B 17/22032* (2013.01); *A61B 2017/00862* (2013.01);
(Continued)

(58) Field of Classification Search
CPC ............... A61F 2/013; A61B 17/22032; A61B 17/2215; A61B 17/22051; A61B 17/00862; A61M 2025/105
See application file for complete search history.

(56) References Cited

U.S. PATENT DOCUMENTS 4,425,908 A 1/1984 Simon
4,643,184 A 2/1987 Mobin-Uddin
(Continued)

FOREIGN PATENT DOCUMENTS

EP 0655228 11/1994
EP 0820729 1/1998
(Continued)

OTHER PUBLICATIONS

Ca Appl. No. 3,029,186, filed Jul. 23, 2016; Office Action dated Feb. 10, 2021.
(Continued)

*Primary Examiner* — Anh T Dang
(74) *Attorney, Agent, or Firm* — Dunlap Codding, P.C.

(57) ABSTRACT

The presently disclosed and/or claimed inventive concept(s) relate, in general, to systems, kits, and techniques for performing embolectomies including, but not limited to, arterial and venous embolectomies.

9 Claims, 7 Drawing Sheets

(51) Int. Cl.
*A61B 17/22* (2006.01)
*A61M 25/10* (2013.01)
*A61B 17/00* (2006.01)

(52) U.S. Cl.
CPC .......... *A61B 2017/2215* (2013.01); *A61B 2017/22051* (2013.01); *A61M 2025/105* (2013.01)

(56) References Cited

U.S. PATENT DOCUMENTS

| | | | |
|---|---|---|---|
| 4,690,672 A | 9/1987 | Veltrup | |
| 4,993,412 A | 2/1991 | Murphy-Chutorian | |
| 5,011,488 A | 4/1991 | Ginsburg | |
| 5,102,415 A | 4/1992 | Guenther et al. | |
| 5,250,060 A | 10/1993 | Carbo et al. | |
| 5,370,609 A | 12/1994 | Drassler et al. | |
| 5,411,509 A | 5/1995 | Hilal | |
| 5,462,529 A | 10/1995 | Simpson et al. | |
| 5,688,234 A | 11/1997 | Frisbie | |
| 5,785,675 A | 7/1998 | Veltrup | |
| 5,814,064 A | 9/1998 | Daniel et al. | |
| 5,833,650 A | 11/1998 | Imran | |
| 5,908,435 A | 6/1999 | Samuels | |
| 5,941,871 A | 8/1999 | Adams et al. | |
| 5,941,896 A | 8/1999 | Kerr | |
| 5,971,938 A | 10/1999 | Hart et al. | |
| 5,972,019 A | 10/1999 | Engelson et al. | |
| 5,989,271 A | 11/1999 | Bonnette et al. | |
| 6,001,118 A | 12/1999 | Daniel et al. | |
| 6,059,814 A | 5/2000 | Ladd | |
| 6,066,149 A | 5/2000 | Samson et al. | |
| 6,080,170 A | 6/2000 | Nash et al. | |
| 6,096,001 A | 8/2000 | Drasler et al. | |
| 6,096,053 A | 8/2000 | Bates | |
| 6,135,977 A | 10/2000 | Drasler et al. | |
| 6,176,844 B1 | 1/2001 | Lee | |
| 6,203,561 B1 | 3/2001 | Ramee et al. | |
| 6,206,868 B1 | 3/2001 | Parodi | |
| 6,221,006 B1 | 4/2001 | Dubrul et al. | |
| 6,238,412 B1 | 5/2001 | Dubrul et al. | |
| 6,245,089 B1 | 6/2001 | Daniel et al. | |
| 6,258,061 B1 | 7/2001 | Drasler et al. | |
| 6,258,115 B1 | 7/2001 | Dubrul et al. | |
| 6,290,710 B1 | 9/2001 | Cryer et al. | |
| 6,325,815 B1 | 12/2001 | Kusleika et al. | |
| 6,325,816 B1 | 12/2001 | Fulton, III et al. | |
| 6,338,735 B1 | 1/2002 | Stevens | |
| 6,346,116 B1 | 2/2002 | Brooks et al. | |
| 6,361,546 B1 | 3/2002 | Khosravi | |
| 6,371,969 B1 | 4/2002 | Tsugita et al. | |
| 6,436,120 B1 | 8/2002 | Meglin | |
| 6,443,972 B1 | 9/2002 | Bosma et al. | |
| 6,447,531 B1 | 9/2002 | Amplatz | |
| 6,450,989 B2 | 9/2002 | Dubrul et al. | |
| 6,454,775 B1 * | 9/2002 | Demarais | A61B 17/320725 606/128 |
| 6,485,500 B1 | 11/2002 | Kokish et al. | |
| 6,485,502 B2 | 11/2002 | Michael et al. | |
| 6,491,660 B2 | 12/2002 | Guo et al. | |
| 6,511,492 B1 | 1/2003 | Rosenbluth et al. | |
| 6,517,551 B1 | 2/2003 | Driskill | |
| 6,524,323 B1 | 2/2003 | Nash et al. | |
| 6,527,746 B1 | 3/2003 | Oslund et al. | |
| 6,544,209 B1 | 4/2003 | Drasler et al. | |
| 6,558,401 B1 | 5/2003 | Azizi | |
| 6,575,996 B1 | 6/2003 | Denision et al. | |
| 6,585,500 B2 | 7/2003 | Park et al. | |
| 6,605,102 B1 | 8/2003 | Mazzocchi et al. | |
| 6,635,070 B2 | 10/2003 | Leeflang et al. | |
| 6,645,222 B1 | 11/2003 | Parodi et al. | |
| 6,652,548 B2 | 11/2003 | Evans et al. | |
| 6,676,637 B1 | 1/2004 | Bonnette et al. | |
| 6,679,893 B1 | 1/2004 | Tran | |
| 6,682,546 B2 | 1/2004 | Amplatz | |
| 6,695,813 B1 | 2/2004 | Boyle et al. | |
| 6,695,858 B1 | 2/2004 | Dubrul et al. | |
| 6,712,835 B2 | 3/2004 | Mazzocchi et al. | |
| 6,726,701 B2 | 4/2004 | Gibson et al. | |
| 6,740,061 B1 | 5/2004 | Oslund et al. | |
| 6,758,855 B2 | 7/2004 | Fulton, III et al. | |
| 6,761,727 B1 | 7/2004 | Ladd | |
| 6,773,448 B2 | 8/2004 | Kusleika et al. | |
| 6,805,864 B1 | 10/2004 | Vinson et al. | |
| 6,814,740 B2 | 11/2004 | McAlister | |
| 6,887,256 B2 | 5/2005 | Gibson et al. | |
| 6,989,019 B2 | 1/2006 | Mazzocchi et al. | |
| 7,011,654 B2 | 3/2006 | Dubrul et al. | |
| 7,163,550 B2 | 1/2007 | Boismier | |
| 7,166,120 B2 | 1/2007 | Kusleika | |
| 7,220,269 B1 | 5/2007 | Ansel | |
| 7,241,304 B2 | 7/2007 | Boyle et al. | |
| 7,241,305 B2 | 7/2007 | Ladd | |
| 7,252,675 B2 | 8/2007 | Denision et al. | |
| 7,344,549 B2 | 3/2008 | Boyle et al. | |
| 7,399,307 B2 | 7/2008 | Evans et al. | |
| 7,491,210 B2 | 1/2009 | Dubrul et al. | |
| 7,494,485 B2 | 2/2009 | Beck et al. | |
| 7,537,601 B2 | 5/2009 | Cano et al. | |
| 7,678,131 B2 | 3/2010 | Muller | |
| 7,717,936 B2 | 5/2010 | Keating et al. | |
| 7,766,936 B2 | 8/2010 | Ladd | |
| 7,780,694 B2 | 8/2010 | Palmer et al. | |
| 7,785,345 B2 | 8/2010 | Ladd | |
| 7,993,302 B2 | 8/2011 | Herbert et al. | |
| 8,252,017 B2 | 8/2012 | Paul, Jr. et al. | |
| 8,444,661 B2 | 5/2013 | Nair et al. | |
| 8,591,540 B2 | 11/2013 | Boyle et al. | |
| 8,740,961 B2 | 6/2014 | Fulton, III | |
| 8,784,442 B2 | 7/2014 | Jones et al. | |
| 8,801,736 B2 | 8/2014 | Vardi | |
| 8,900,257 B2 | 12/2014 | Straub et al. | |
| 9,827,084 B2 | 11/2017 | Bonnette et al. | |
| 2001/0012951 A1 | 8/2001 | Bates et al. | |
| 2002/0016565 A1 | 2/2002 | Zadno-Azizi et al. | |
| 2002/0026145 A1 | 4/2002 | Bagaoisan et al. | |
| 2002/0026203 A1 | 4/2002 | Bates et al. | |
| 2002/0068954 A1 | 6/2002 | Foster | |
| 2002/0169458 A1 | 11/2002 | Connors | |
| 2003/0114879 A1 | 6/2003 | Euteneuer et al. | |
| 2003/0187475 A1 | 10/2003 | Tsugita et al. | |
| 2005/0055047 A1 | 3/2005 | Greenhalgh | |
| 2005/0159772 A1 | 7/2005 | Lowe et al. | |
| 2005/0192620 A1 | 9/2005 | Cully et al. | |
| 2006/0030877 A1 | 2/2006 | Martinez et al. | |
| 2006/0135987 A1 | 6/2006 | Jones et al. | |
| 2006/0200191 A1 | 9/2006 | Zadno-Azizi | |
| 2006/0253145 A1 | 11/2006 | Lucas | |
| 2007/0060942 A2 | 3/2007 | Zadno-Azizi | |
| 2007/0088383 A1 | 4/2007 | Pal et al. | |
| 2007/0167974 A1 | 7/2007 | Cully et al. | |
| 2007/0191878 A1 | 8/2007 | Segner et al. | |
| 2007/0208351 A1 | 9/2007 | Turner | |
| 2008/0234722 A1 | 9/2008 | Bonnette et al. | |
| 2009/0069828 A1 | 3/2009 | Martin et al. | |
| 2011/0040319 A1 * | 2/2011 | Fulton, III | A61F 2/013 606/194 |
| 2012/0130395 A1 † | 5/2012 | Vardi | |
| 2013/0310803 A1 | 11/2013 | Morsi | |
| 2015/0305756 A1 * | 10/2015 | Rosenbluth | A61B 17/320725 606/159 |
| 2015/0313732 A1 | 11/2015 | Fulton | |

FOREIGN PATENT DOCUMENTS

| | | |
|---|---|---|
| EP | 1545388 | 5/2009 |
| FR | 2580504 | 10/1986 |
| FR | 2694687 | 2/1994 |
| WO | 9922673 | 5/1999 |
| WO | 20010115629 | 8/2001 |
| WO | 2008036156 | 3/2008 |
| WO | 2008151204 | 12/2008 |

(56) References Cited

FOREIGN PATENT DOCUMENTS

| WO | 2014081892 | 5/2014 |
|----|------------|--------|
| WO | 2017019572 A1 | 2/2017 |

OTHER PUBLICATIONS

PCT/US2016043769, International Search Report and Written Opinion, dated Sep. 29, 2016.
Saab, Mark A., "Applications of High-Pressure Balloons in the Medical Device Industry", Vention Medical. (2015).

\* cited by examiner
† cited by third party

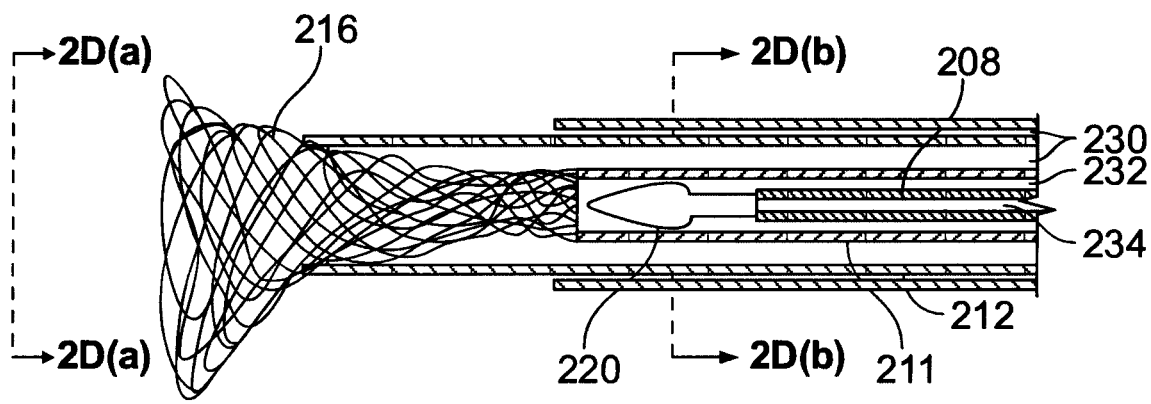
FIG. 2C
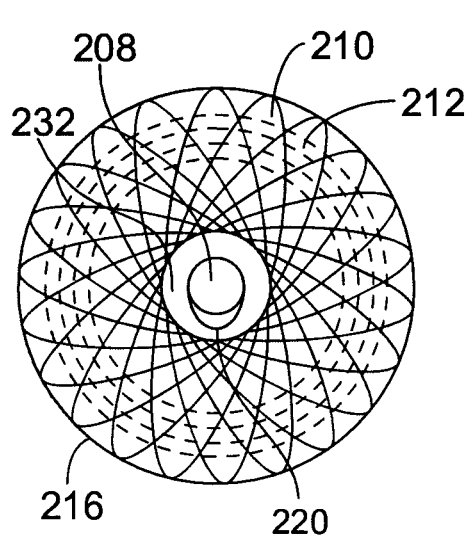
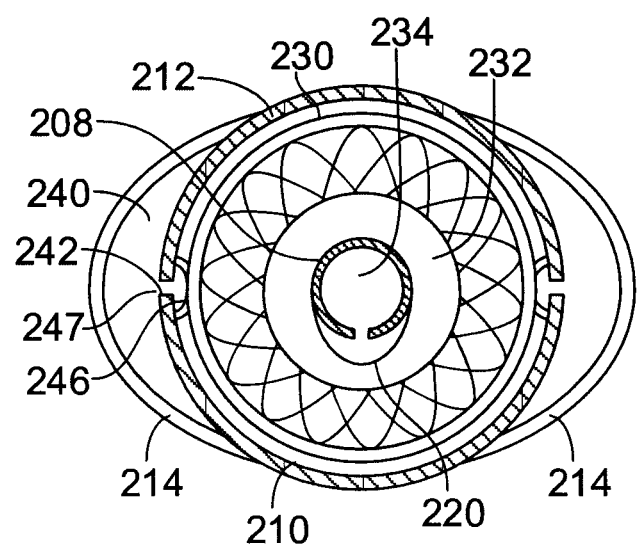
FIG. 2D(a)  FIG. 2D(b)

EMBOLECTOMY SYSTEM AND METHODS OF MAKING AND USING SAME

CROSS REFERENCE TO RELATED APPLICATIONS

This application is a U.S. national stage application filed under 35 U.S.C. § 371 of International Application No. PCT/US16/43769, filed Jul. 23, 2016, which claims priority under 35 U.S.C. § 119(e) from provisional application No. 62/196,881, filed Jul. 24, 2015. The entire contents of the above-referenced patent applications are hereby expressly incorporated herein by reference in their entirety.

TECHNICAL FIELD

The presently disclosed and/or claimed inventive concept(s) relate, in general, to systems, kits, and techniques for performing embolectomies including, but not limited to, arterial and venous embolectomies.

BACKGROUND

The human circulatory system relies upon the heart to act as a pump and thereby provide motive force for circulating blood through vasculature. This vasculature carries the blood to tissues that obtain oxygen and nutrients from the blood (the arterial system), and returns carbon dioxide and wastes to the returning bloodstream (the venous system). A loss of regular circulation of blood to any bodily tissue will generally result in impairment or death of the tissue—whether the tissue is in the brain (leading to a stroke) or the heart (leading to coronary artery disease and heart attack). The inability of the vasculature to circulate blood is commonly caused for example, but not by way of limitation, the build-up of plaque inside the vasculature thereby causing a partial or complete blockage, hardening, and/or inflammation of the vasculature.

Blockages can be reduced or eliminated via a number of techniques. For example, but not by way of limitation, angioplasty is a procedure by which a catheter is introduced into an artery and a balloon associated with the catheter is thereafter inflated outwardly to compress plaque against the vessel walls, enlarging the vasculature path, and restoring blood flow. Devices, such as stents, may thereafter be inserted into the vasculature in order to maintain it in its open state. If the blockage is severe, a bypass may be required whereby real or synthetic vasculature is attached to the human vasculature and blood flow is routed around the blockage. By way of atherectomy procedures, the build-up catheters have also been used to deliver therapeutic medications into a clot to dissolve it, for example.

Similarly, embolectomy procedures remove emboli or clots in the vasculature—either arterial or venous—that block blood flow. Embolectomies generally involve moving a deflated balloon (e.g., a Fogarty) through and beyond a clot, inflating the balloon, and drawing the balloon backward to pull the clot out of the body. Alternatively, clots may be removed via aspiration embolectomy which uses suction to remove clots from the vasculature of a patient.

It is to a new embolectomy system that may be used in either the arterial or venous vasculature systems that the presently disclosed and/or claimed inventive concept(s) is directed.

SUMMARY

This document describes systems and techniques by which a physician may execute an embolectomy for example, but not by way of limitation, a peripheral embolectomy on a patient, including human and other animal patients. In one example comprising a peripheral embolectomy, a catheter is introduced into a patient at a first peripheral artery, extended across the patient's midline, and then into the other peripheral artery. The catheter may have an inner lumen through which a capture device may be passed, on the distal end of a hollow shaft. The capture device may be a structure that naturally expands to at least the diameter of the relevant vasculature being treated so as to form a skirt that blocks the passage of debris, along with a capture sleeve that surrounds the expanding portion of the capture device. The capture sleeve may surround the expanding portion of the capture device to hold it in a compressed position with a small outer diameter. The capture sleeve thereafter can be withdrawn proximally so that the expanding portion slides out a distal end of the capture sleeve and naturally expands to a larger outer diameter.

The compression device may, in turn, be extended past the capture device and the blockage, and may draw debris into the capture device by being expanded against the inner wall of the vasculature and pulled back proximally. The capture device may include, for example, a naturally-expanding mesh structure made of nitinol or similar wire, and such wire may be bare or may be covered by a fabric such as PTFE fabric. In certain implementations, a balloon of the catheter may be anchored in a first branch of vasculature, and the capture device may be positioned in a second branch that is a sub-branch of the first branch. The compression device may operate on the blockage in the second branch or in a sub-branch of the second branch.

When the catheter is in position just proximal of the area to be treated, the capture device can be extended out of the distal end of the catheter and may be allowed to naturally expand to contact the vessel walls thereby blocking off the vessel (though perhaps permitting flow of blood cells and plasma between wires of the mesh in an embodiment where the capture device is a mesh device). The expansion may occur immediately upon exiting the distal end of the catheter, or after the capture device has been extended down the vasculature to another location. Before or after the extension of the capture device beyond the distal end of the catheter, the catheter itself may be fixed and anchored in the vessel by expanding a device, such as a balloon, radially from an outer periphery of the catheter. The radial balloon may extend along a relatively short length of the catheter near the distal end of the catheter for example, but not by way of limitation.

A compression device may also be extended out of a distal end of the capture device, such as through a cannula in the middle of the hollow shaft that holds the capture device and is positioned through the center of the capture device. The compression device may be provided with a laterally extending element, such as a balloon mounted around a shaft or to one side of a shaft, and may be initially unextended when inside the hollow shaft and the catheter. The shaft for the compression device may itself be hollow and, after the laterally extending element has moved linearly out of the catheter and capture device, air pressure or other fluid pressure may be introduced at a proximal end of the inner shaft from outside the patient so as to extend the element laterally away from the shaft and outward against the walls of the vasculature. Such extension may occur after the element has been slid linearly past the blockage, and the element may then be drawn backward across the blockage and toward the capture device while the element is maintained in its extended position. The compression device may then be pulled back to its unextended position, moved linearly past the blockage again, extended, and pulled toward the capture device again. Such a process may be repeated a needed number of times as necessary to remove the blockage and/or restore blood flow within the vasculature. Also, the compression device and capture device can be drawn back inside the outer catheter, the anchoring of the outer catheter may be removed, and the end of the outer catheter may be moved linearly through the vasculature to an area just short of a secondary blockage, with the steps just described being repeated for removal or other treatment of the secondary blockage.

The drawing of the compression device toward the capture device may cause debris to be dislodged from the vasculature, and the debris may be funneled by the compression device into the cannula, or the debris may become entangled by the capture device. A low level of suction may be maintained on the cannula to draw such debris out of the patient and additional debris may be removed when the compression device and capture device are removed from the catheter and brought outside the patient's body before the outer catheter itself is withdrawn from the patient's body.

In certain implementations, such systems and technique may provide one or more advantages. For example, such a relatively straightforward technique utilizing the presently disclosed and/or claimed inventive concept(s) may result in less wound infection and other problems created by a need for an incision in surgical embolectomy (e.g., femoral nerve injury, lymphocele, and seroma). Furthermore, the presently disclosed and/or claimed inventive concept(s) may permit treatment of larger vessels than traditional suction mechanical/embolectomy that involve stent retrievers designed for clot removal in the cerebral vasculature, and percutaneous mechanical thrombectomy devices. In addition, the presently disclosed and/or claimed inventive concept(s) may avoid renal insufficiency limitations of pulse spray aspiration catheters. In certain embodiments, the presently disclosed and/or claimed inventive concept(s) may avoid or reduce bleeding complications of clot dissolving medications used, for example, with infusion catheters.

The presently disclosed and/or claimed inventive concept(s) may also comprise applying one or more drugs to an inner vascular wall by pressing drug-provided portions of the compression device against the vascular wall. In addition, the method may comprises repeatedly: (a) advancing the compression device distally past a vascular blockage in a vessel, (b) radially expanding the compression device against an inner wall of the vessel, (c) proximally drawing the compression device across the blockage, and (d) radially contracting the compression device away from the inner wall of the vessel. And the method can also include identifying that a blockage has occurred as a result of a medical procedure performed on a patient, identifying a location of the blockage in a lower extremity of the patient, and performing the method in the identified blockage at the identified location.

In yet another implementation, a kit for performing endovascular surgery is disclosed. The kit comprises an outer catheter having a proximal end and a distal end and defining a cannula; a sleeve sized to fit inside an interior cannula of the outer catheter, arranged to slide longitudinally in the outer catheter, and having an open distal end; an expandable capture device located inside the sleeve and sized to be advanced through the sleeve and the cannula defined by the outer catheter, the expandable capture device including an introduction shaft arranged to push the expandable capture device along a length of the catheter and out the open distal end of the sleeve, wherein the expandable capture device is arranged to expand radially outward when not being held inward by the sleeve; and a compression device located separate from and not inside the outer catheter and expandable capture device, and sized to pass through a cannula in the introduction shaft, to be slid linearly out of the catheter and past the expandable capture device, and to be expanded radially outward and drawn backward toward the expandable capture device. At least two of the outer catheter, sleeve, expandable capture device, and compression device may be located separate from each other and each of the outer catheter, sleeve, expandable capture device, and compression device are located in a common package for access by a physician.

The details of one or more embodiments of the presently disclosed and/or claimed inventive concept(s) are set forth in the accompanying drawings and the description below. Other features and advantages will be apparent from the description and drawings, and from the claims.

DESCRIPTION OF THE DRAWINGS

FIG. 2C is a side cross-sectional view of the components of the peripheral embolectomy system of FIG. 2A.

FIG. 2D is a cross-sectional view transverse to a longitudinal length of the peripheral embolectomy system of FIG. 2C.

DETAILED DESCRIPTION

Figure 1:
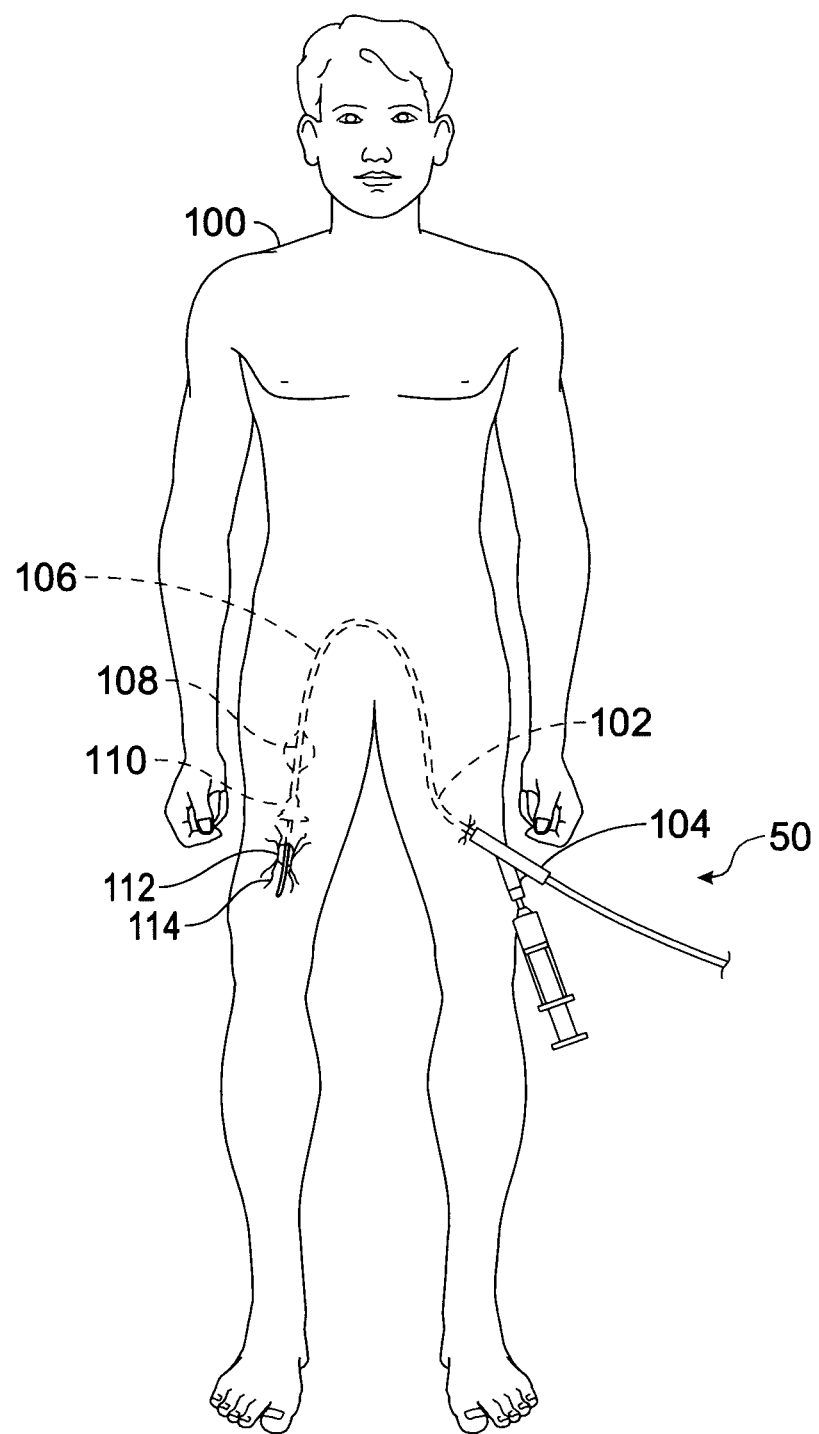
FIG. 1 is an illustration of a patient having a peripheral embolectomy performed utilizing an embodiment of the presently disclosed and/or claimed inventive concept(s).

Before explaining at least one embodiment of the presently disclosed inventive concept(s) in detail, it is to be understood that the presently disclosed inventive concept(s) is not limited in its application to the details of construction and the arrangement of the components or steps or methodologies set forth in the following description or illustrated in the drawings. The presently disclosed inventive concept(s) is capable of other embodiments or of being practiced or carried out in various ways. Also, it is to be understood that the phraseology and terminology employed herein is for the purpose of description and should not be regarded as limiting. Like reference symbols in the various drawings indicate like elements.

Unless otherwise defined herein, technical terms used in connection with the presently disclosed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed herein can be made and executed without undue experimentation in light of the present disclosure. While the articles and methods of the presently disclosed inventive concept(s) have been described in terms of preferred embodiments, it will be apparent to those of skill in the art that variations may be applied to the articles and/or methods and in the steps or in the sequence of steps of the method described herein without departing from the concept, spirit, and scope of the presently disclosed inventive concept(s). All such similar substitutes and modifications apparent to those skilled in the art are deemed to be within the spirit, scope, and concept of the presently disclosed inventive concept(s).

As utilized in accordance with the present disclosure, the following terms, unless otherwise indicated, shall be understood to have the following meanings:

The use of the word "a" or "an" when used in conjunction with the term "comprising" in the claims and/or the specification may mean "one", but it is also consistent with the meaning of "one or more," "at least one," and "one or more than one." The use of the term "or" in the claims is used to mean "and/or" unless explicitly indicated to refer to alternatives only or that the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example, unless specifically disclosed and discussed to the contrary.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "associate" as used herein will be understood to refer to the direct or indirect connection of two or more items.

The presently disclosed and/or claimed inventive concept(s) generally relates to systems, kits, and techniques for performing embolectomies for example, but not by way of limitation, peripheral embolectomies in the lower extremities of a human patient. Such techniques may include introducing a catheter into an incision in a femoral artery of a patient and advancing the catheter across to the other femoral artery of the patient. The catheter may then be anchored in position proximate to an identified blockage in the second femoral artery or in vasculature that is distal from the second femoral artery, and a funnel or other debris-capturing device may be extended from a distal end of the catheter. The funnel may be disposed in a sleeve that is also extended from the distal end of the catheter. In this manner, the funnel may be located in the vasculature independent of the location of the end of the catheter. In one embodiment, the distal end of the catheter is anchored in a first branch of the vasculature and the funnel is extended from the sleeve in a sub-branch of the vasculature where it may naturally expand against the walls of a vessel and fill the cross-sectional area of the vessel so as to capture debris flowing through the vessel.

A compression device may then be extended in a direction distal from a distal end of the debris-capturing device and may be expanded against the walls of the vasculature at a location of an identified blockage. The compression device may then be drawn backward toward the debris-capturing device (e.g., the funnel and sleeve) in its expanded state so as to simultaneously compress material against the wall of the vessel, and to also pull backward on material that may break free from the wall of the vessel. Such motion may pull the debris into the debris-capture device from which it may be further routed into the catheter and drawn outside the body for disposal. Also, medications may be applied to the vessel at and around the location of the blockage, including clot dissolving medications and anti-restenosis medications. Moreover, the method just described can be followed up with the placement of one or more stents to assist in keeping the vessel open in the future. In this manner, the presently disclosed and/or claimed inventive concept(s) may permit for relatively simple and inexpensive minimally invasive approaches for clearing blockages in vasculature—e.g., peripheral arteries and/or veins.

FIG. 1 is a conceptual diagram of a patient 100 having a peripheral embolectomy performed thereon utilizing an embolectomy system 50 according to the presently disclosed and/or claimed inventive concept(s). Generally, the patient 100 will be placed under local or general anesthesia and be positioned (in a prone or supine position for venous procedures and a supine position for arterial procedures) in an appropriate operating or procedure suite in a healthcare facility. The particular arrangement of the patient 100 and the embolectomy system 50 of the presently disclosed and/or claimed inventive concept(s) are shown in a simplified illustration solely for purposes of clarity.

As shown in FIG. 1, the embolectomy system 50 generally comprises a catheter 102 associated with a Y-connector 104. The catheter 102 is shown as having been inserted into an incision in a thigh of the patient 100 and introduced into the patient's femoral artery in a conventional manner. The catheter 102 includes a sheath 106, an expandable portion 108, a capture device 110, a compression device 112, and a guide wire 114. The sheath 106 is advanced through the incision, along the artery, across the common iliac artery, and down through a second femoral artery in the leg opposite where the insertion incision was made. For example, the sheath 106 may be introduced into the right femoral artery and advanced into the left femoral artery through the common iliac artery or, alternatively, the sheath 106 may be introduced into the left femoral artery and advanced into the right femoral artery. The femoral artery into which the sheath 106 of the catheter 102 is introduced is generally the femoral artery opposite the side of the body in which a blockage has been identified and as being in need of clearing.

The sheath 106 of the catheter 102 may be advanced through the femoral arteries along a guide wire 114 which may assist in steering the catheter 102 through the common iliac artery and into the second femoral artery, for example, but not by way of limitation. The guide wire 114 may initially be introduced through an inflation port of the Y-connector 104 in a conventional manner, steered up the first femoral artery, across the common iliac artery, and into the second femoral artery until it passes by a location at which the blockage has been identified. The catheter 102 may then be advanced in the same opening around the guide wire 114 and may follow the guide wire 114 along its path within the body. The catheter 102 is generally advanced through the body and along the guidewire 114 until it is proximal to both the location of the blockage and the distal end of the guide wire. When the catheter 102 is in the proximal position, the guide wire 114 may be left in place or withdrawn.

Components for performing the procedure may be located inside the sheath 106 (i.e., the components may be "nested" within the sheath 106) and may be advanced along with the sheath 106 as it is introduced to the site of the blockage. Alternatively, these components may be introduced to the site of the blockage after the sheath 106 is put into place. Such components, for example, may include the expandable portion 108, the capture device 110, and the compression device 112. The compression device 112 may take a variety of forms that are capable of expanding and contracting radially along a longitudinal axis. For example, the compression device 112 may include spreading leafs at its terminal end that are capable of being spread open and biased against the walls of the vasculature. Alternatively, the compression device 112 may include one or more balloons at the terminal end of the catheter 102 that can be inflated and deflated so as to bring it in contact with the walls of the vasculature.

The capture device 110 may take the form of a funnel-shaped structure, for example but not by way of limitation, and an embodiment thereof may comprise a nitinol mesh structure in certain embodiments. In such an embodiment, the capture device 110 is capable of being selectively expanded outward and can thereafter be selectively collapsed by a physician performing a procedure. The capture device 110 may be formed in any variety of manners known in the art, including by bending nitinol wire to create a natural funnel shape and thereafter heating the wire in that form to provide it with shape memory. The capture device 110 may also be coated with one or more chemicals and may also be surrounded by or filled with a fabric, such as a PTFE fabric, to fill gaps between individual wires in the mesh. The internodal distance for the fabric may be selected so as to permit the passage of plasma and red blood cells but not allow for the passage of debris past the capture device 110 and into the vasculature proximal the capture device 110.

The catheter 102 may also be provided with an expandable portion 108 about its periphery. The expandable portion 108 may, in one embodiment, be an expandable balloon that is capable of being inflated to thereby press against the walls of the vasculature. In this manner, the catheter 102 is held in place and thereby preventing from moving longitudinally within the vasculature. The expandable portion 108 may also act to impede blood flow and to provide a barrier against debris that may escape the capture device 110. With the catheter 102 anchored in this manner, the sheath 106 may be advanced out of a distal end of the catheter 102. The capture device 110 may be positioned inside the, sheath 106 and the capture device may move longitudinally with or independently of the sheath 106. The sheath 106 may then be positioned at a location proximal a blockage so that the capture device 110 may be extended from the distal end of the sheath 106. The capture device 110 may thereafter be expanded radially outward against the wall of the vasculature to fill the cross-section of the vessel proximal to the blockage.

As described in more detail below, the guide wire 114, the catheter 102, and the sheath 106 may initially be inserted into the patient and advanced to their appropriate positions within the patient 100 and relative to the blockage. The capture device 110 may then be extended from the distal end of the sheath 106 which may, by itself, cause the capture device 110 to expand outward against the walls of the vasculature. Alternatively, a mechanism may be provided to hold the capture device 110 in a closed position until it has been advanced sufficiently from the sheath 106, at which point it may be radially expanded against the wall of the vasculature. The compression device 112 may then be extended along the guide wire 114 (if the guide wire 114 has been left in place) to a position distal the blockage. The capture device 110 may have been advanced to the distal end of the catheter 102 along with the sheath 106 or the capture device 110 may have been advanced after the sheath 106 was advanced into place. One of ordinary skill in the art will recognize that the order in which the components are advanced through the vasculature is a task is variable and is, in many circumstances, a matter dictated by the patient's physiology.

The compression device 112 may then be expanded to compress against the walls of the vasculature. Such compressive action may help move plaque or other material radially outward and against the wall of the vasculature so as to open up the vasculature in a greater manner and thereby restore proper blood flow. While the compression device 112 is maintained in its expanded state, the compression device 112 may be pulled proximally toward the distal end of the catheter 102 so as to drag an outer surface of the compression device 112 against and through the blocking material. Such action may cause the blocking material to be compressed against the wall of the vasculature so as to open the vasculature and thereby restore blood flow. Alternatively and/or in addition thereto, such movement of the compression device 112 may also cause portions of the blocking material to become dislodged so as to further open the vasculature. The dislodged portions of the blocking material, in the form of debris, may move upstream in the femoral artery and be captured by the capture device 110. Portions of the debris may be drawn toward an internal portion of the capture device 110 when the capture device 110 is in the form of a funnel. Such debris may then be drawn into the catheter 102 and aspirated out of the patient 100 in a conventional manner.

Radiopaque materials, marker bands, or other types of fluorescing markers may also be associated with one or more of the components of the embolectomy system 50 to assist a physician in visualizing and/or locating the respective components within the patient 100 during a procedure. Such markers will be readily visible via well-known patient imaging systems. For example, in one embodiment the expandable portion 108 may have a marker band placed at its midpoint, at each of its ends, and/or at one or more locations along its length that outline or denote the beginning and end contact of the expandable portion 108 with the walls of the vasculature when it is in an expanded state. A marker band may also be placed on or near the distal end of the sheath 106 inside the catheter 102 so that the progress of the sheath 106, and the location at which the capture device 110 will expand when extended out the distal end of the sheath 102 may also be tracked as the sheath 106 is extended. Another marker band may be located on a proximal end of the capture device 110 so as to allow a physician to monitor the relative extension and placement of the capture device 110 out of the sheath 106. The capture device 110 may also be marked in appropriate circumstances and, if made from a nitinol mesh which is radiopaque, will be at least partially visible under fluoroscopy. Alternatively, in another embodiment the capture device 110 may be coated with a material that increases its imaging visibility. For example, the distal end of the capture device 110 may be coated with a material such that the degree of radial expansion of the capture 110 can be actively visualized and tracked. In another embodiment, the sheath 106 also has a band placed at its distal end such that the band may be visualized relative to a band at or near the: (i) proximal end of the capture device 110; or (ii) a band on the outer portion of the catheter 102 to judge when the sheath 106 has been extended close to the blockage and when capture device 110 has been extended an appropriate length (i.e., when the band on the distal end of the sheath 106 overlaps with the band on the capture device 110 proximal end).

Any of the components of the embolectomy system 50 may be associated with one or more therapeutic compounds. The compression device 112, for example in one non-limiting embodiment, may be drug-coated or drug eluting such that the compression device 112 emits a therapeutic amount of a medicine and/or presses a therapeutic amount of a medicine into the wall of the vasculature as the compression device 112 is pulled through the blockage and/or vasculature. For example but not by way of limitation, the compression device 112 may be coated with (or otherwise be associated with) a therapeutic amount of an anti-clotting medicine and/or a medicine to prevent restenosis of the vessel (for example, but not by way of limitation, paclitaxel, docetaxel, sirolimus, and combinations thereof).

In certain circumstances, the presently disclosed and/or claimed inventive method may be preceded by an identification of the existence and location of a clot in the patient's vasculature. For example, a clot may exist and be identified by ordinary diagnosis upon the patient 100 visiting a physician. In another example, a clot may be created by the performance of another procedure, such as the insertion of a stent in a remote location of the patient's vasculature. In such a situation: (A) a determination may be made that a peripheral blockage has occurred in response to the performance of a procedure; (B) the location of the blockage may be identified; and (C) performance of the embolectomy method using embolectomy system 50 may be instituted.

The embolectomy method using the embolectomy system 50 as described herein may also be followed by one or more other procedures. For example but not by way of limitation, the presently disclosed and/or claimed embolectomy method may be used to at least temporarily clear a blockage. If the presently disclosed and/or claimed embolectomy method is thereafter determined to be insufficient, additional techniques may be used to achieve a satisfactory result—e.g., the insertion of one or more stents in the vasculature. Also, some procedures traditionally involve the use of very long stents (e.g., equal or greater than 200 cms). Using the embolectomy methods described herein, a "focal lesion" approach may be used for stenting thereby resulting in the opening of the blocked areas, the identification of the areas that had the most blockage, and/or the identification of the areas most in need of additional support such as in the form of stenting. For example, a vessel with 10 cm of blockage may have had two areas with particularly severe blockage. In such a situation, two shorter stents (e.g., 1-2 cm each) may be placed in the two areas with particularly severe blockage instead of a longer 10 cm stent across the entirety of the blockage. As such, the locations along the vessel most in need of additional support may be identified and appropriately addressed. Such identification may be accomplished in a number of ways, including by imaging and/or by observing the forces applied to the compression device 112 (or other component of the embolectomy system 50) during the presently disclosed and/or claimed embolectomy methods.

The size and/or shape of vessels that may be addressed by the presently disclosed and/or claimed embolectomy system 50 and methods is relatively large and is a significant advantage of the presently disclosed and/or claimed inventive concept(s). For example, vessels having a diameter of 2 mm to 8 mm or even larger may be addressed. In some implementations, the systems and techniques described herein may be applied to vessels having a normal unblocked diameter of 4 mm to 6 mm, 4 mm to 8 mm, 6 mm to 8 mm, and diameters greater than 8 mm. It is anticipated that when the embolectomy system 50 is used in an embodiment for a peripheral arterial embolectomy, vessels having a normal unblocked diameter of from about 2 mm to about 10 mm are treatable and, when used for a peripheral venous embolectomy, vessels having a normal unblocked diameter of from about 2 mm to about 16 mm are treatable.

Figure 2A:
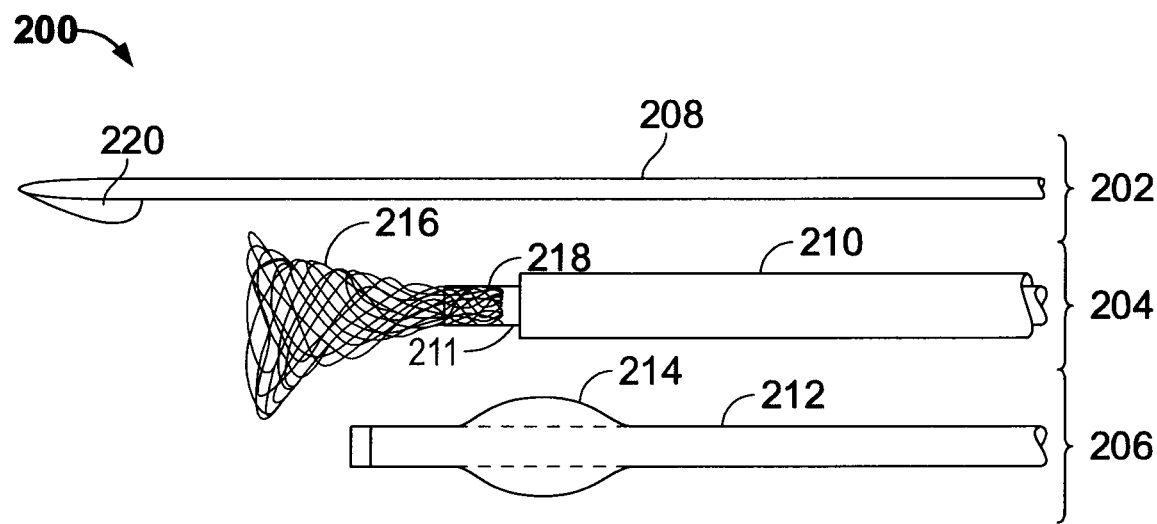
FIG. 2A is a side perspective view of the components of a peripheral embolectomy system according to an embodiment of the presently disclosed and/or claimed inventive concept(s).

FIG. 2A shows the components of one particular embodiment of the embolectomy system 50—i.e., a peripheral embolectomy system 200 that may be inserted into the peripheral arterial vasculature of a patient. The components are shown here as three separate subsystems adjacent to each other for clarity, though in normal implementation the components would be deployed coaxially with one another with each subsequent subsystem surrounding the prior subsystem—i.e., the components are nested within one another. In the peripheral embolectomy system 200, the three subsystems include a compression system 202, a capture system 204, and an outer catheter system 206.

Referring now to the compression system 202, the compression system 202 comprises a catheter shaft 208 and a compression device 220 (shown in FIG. 2A as an expandable balloon for example but not by way of limitation) near a distal end of the catheter shaft 208. In one embodiment, the compression system 202 may be a rapid exchange catheter provided with the compression device 220 in the form of a 3 mm×10 mm compliant balloon. A rapid exchange catheter provides a very rapid, atraumatic means of exchanging one balloon dilatation catheter or other device for another balloon dilatation catheter or other device and such rapid exchange catheters are generally known in the art.

The compression device 220 may be located axially around an outer periphery of the catheter shaft 208. The compression device 220 may also be pneumatically connected to a lumen that runs longitudinally along an interior or exterior surface of catheter shaft 208 and whose other end terminates at a proximal end of the catheter shaft 208 which may be located outside the patient. The lumen allows air or other fluid to be supplied from an exterior of the patient in order to inflate the compression device 220 after it has been located within the vasculature. In an embodiment, the compression device 220 may be made from PELLETHANE™ (Lubrizol Corporation, Wickliffe, Ohio) and may be capable of inflating to 8 mm in diameter (or in a range of a selected maximum inflation diameters of 4, 6, 8, 10, or 12 mm or greater in diameter). The compression device 220 is located close to the distal end of the catheter shaft 208, and may be centered about a platinum/iridium marker band associated with the catheter shaft 208 so as to better visualize the placement of the components of the compression device 220 within the vasculature.

In alternative embodiments, the compression device 220 may take forms other than a balloon so long as the compression device 220 is capable of expanding and contacting the inner walls of the vasculature. The compression device 220 in the embodiment shown in FIG. 2A is pliable and/or compressible (i.e., sized and/or shaped) so as to be able to fit inside the capture system 204 and the outer catheter system 206 for introduction into a patient. For example, but not by way of limitation, the compression device 220 may comprise a plurality of expandable leaflets that pivot outward from the periphery of the catheter shaft 208 and are capable of pushing outward against the inner wall of the vasculature. Depending on the particular use of the peripheral embolectomy system 200, the leaflets may extend radially outward and engage smoothly along the inner surface of the vascular wall when withdrawn proximally. In an alternative embodiment, the leaflets may extend radially outward and engage the inner surface of the vasculature wall such that they "bite" into the inner wall more forcefully thereby dislodging or scraping the clot debris from the inner wall. The terminal ends of the leaflets may be sized and/or shaped (e.g., rounded) to control the level of disruption or engagement with the blocking material. The force that a physician applies to radially expand the leaflets outward and engage the inner wall of the vasculature is also controllable by the physician. In such an implementation, the leaflets may be expanded by air pressure delivered down or through the catheter shaft 208 (e.g., via a lumen within or on an outer surface of the catheter shaft 208) or by mechanical action of a wire, thread, or rod moving in the catheter shaft 208 to thereby open the leaflets outward and in engagement with the inner wall of the vasculature.

The compression device 220 may also include multiple balloons arranged longitudinally relative to each other and each balloon may be in fluid engagement with the outside of a patient so as to be inflatable together or individually (or in various combinations) via an inflation source located outside the patient and controlled by the physician. For example in one non-limiting embodiment, each balloon may be slightly larger in diameter toward the distal end of the compression system 202, so that as the compression device 220 is pulled proximal, each successive balloon provides slightly more force outward against the vessel wall than did the immediately prior balloon. In an alternative embodiment, the compression device is a single balloon that may be progressively inflated and expanded to have an increasing diameter as the compression device 220 is moved proximal. In this manner the compression device 220 presses with increasingly greater radial force against the vessel wall as the compression device 220 is drawn proximally. In an alternative embodiment, the compression device 220 may have a cone or wedge-shaped leading edge (when pulled proximally) such that increasing levels of radial force is applied to any specific location on the vessel wall as the compression device 220 is pulled proximally.

In a non-limiting embodiment, the compression system 202 may be arranged so that the peripheral embolectomy system 200 is compatible with for example, but not by way of limitation, 0.038", 0.035", 0.025", 0.018" or 0.014" guide wires. The catheter shaft 208 may have, for example, a 133 cm working length (or a working length of about 100, 110, 120, 130, 140, 150, or 160 cm), with an outer diameter of 0.048" (or about 0.040, 0.045, 0.050, or 0.55 inches). The catheter shaft 208 may be constructed with an extruded dual lumen PELLETHANE™ (Lubrizol Corporation, Wickliffe, Ohio) shaft where one lumen may make up the main structure of the catheter shaft 208, and the other may comprise an inflation/deflation lumen. The compression device 220 may be thermally bonded to the catheter shaft 208 and have a luer attached to its proximal end with adhesive. The compression device 220 may project wholly or partially off of or away from a distal end of the catheter shaft 208 and, in such an embodiment, the compression device 220 may be wholly or at least partially attached to the terminal end of the catheter shaft 208. In alternative embodiments, the compression device 220 may be attached to a side of the catheter shaft 208 at or near the distal end of the catheter shaft 208.

The capture system 204, as shown in the embodiment of FIG. 2A, may comprise a capture sleeve 210 (which, in one embodiment is a polyimide material) and a shaft 211. At the distal end of the shaft 211 an expanding funnel 216 is associated with the shaft 211 at a bonded region 218. The shaft 211 may be located inside and longitudinally slidable within the capture sleeve 210. The working length of the capture system 204 may be 90 cm (or a working length of about 40, 50, 60, 80, 85, 90, 95, 100, 105, 110, 115, 120, or 125 cm, for example but not by way of limitation), with a major outer diameter of 0.098" (or about 0.085, 0.090, 0.095, or 1.00 inches), and an inner diameter of 0.065" (or about 0.055, 0.060, 0.065, 0.070, or 0.074 inches).

When the capture sleeve 210 is moved forward in the vasculature, the expanding funnel 216 (which is held in place within the capture sleeve 210 by friction around its outer edge engaged with the inner wall of the capture sleeve 210) may move alone or in conjunction with the capture sleeve 210. The capture sleeve 210 may be extended out of a distal end of the guide catheter 212 of the catheter system 206. When the capture sleeve 210 is moved proximally back toward the end of the guide catheter 212 and the expanding funnel 216 is left in its longitudinal position, the expanding funnel 216 is exposed and allowed to expand radially against the inner wall of a vessel. Controlling the position of the capture sleeve 210 allows the user/operator to control the exposed length of the expanding funnel 216, and thus control its diameter and opening angle (i.e., the spread between opposed sides of the funnel wall). The capture sleeve 210 can be locked in place by tightening a touhy borst valve for example located on the proximal end of the guide catheter 212. The capture sleeve 210 has an internal step in internal diameter that stops the capture sleeve 210 from moving too far forward when it contacts a ledge created by the attachment point between the expanding funnel 216 and the shaft 211.

The shaft 211 of the capture sleeve 210 may be made from any biocompatible material. In one embodiment, for example but not by way of limitation, the shaft 211 is made by reflowing a VESTAMID™ (Evonik Industries) extrusion over stainless steel braid and a polytetrafluoroethylene (PTFE) liner. The braid may be formed by taking a number of strands (e.g., 16 or 32 strands) of nitinol, steel or aluminum type wire braided to a desired maximum funnel outer diameter. In one non-limiting embodiment the expanding funnel 216 has an outer diameter of 8 mm however could be braided and shaped to an outer diameter of 14 mm. The braid comprising the expanding funnel 216 can then be inverted back through its inner diameter and heat set into the desired shape—e.g., a funnel shape. The expanding funnel 216 may then be placed over the shaft 211 and fixed with a radio opaque marker band at the proximal end of the expanding funnel 216 taper, onto the distal end of the shaft 211, and/or on the capture sleeve 210. The proximal ends of the nitinol strands of the expanding funnel 216 may, in one example, be associated with a distal end of the shaft 211 in the bonded region 218 (e.g., via a PEBAX™ (Arkema Group) extrusion bonding) thereby fixing the expanding funnel 216 in place on the shaft 211.

The capture sleeve 210 may, in one non-limiting embodiment, comprise two polyimide tubes, with a larger inner diameter polyimide tube slid over a smaller polyimide tube, wherein these nested tubes may be adhesively bonded over a short length thereof. Much of the length of the capture sleeve 210 arises from the smaller polyimide tube, and the transition of the two polyimide tubes creates a ledge that contacts the bonded nitinol strands so that the capture sleeve 210 may only extend distally until the ledge makes contact with the proximal end of the expanding funnel 216. The capture sleeve 210 may include a luer adhesively bonded on a proximal end of the capture sleeve 210. A touhy borst valve may be attached to that luer. The capture sleeve 210 may then be slid over the shaft 211 and the luer may be adhesively bonded on the proximal end of the shaft 211. The capture sleeve 210 may be non-removably fixed between the proximal end of the expanding funnel 216 and such proximal luer.

Turning now further to the outer catheter system 206, in one non-limiting embodiment, the outer catheter system 206 may comprise a guide catheter 212 having an occlusion balloon 214 positioned along its length. The outer catheter system 206 has a working length of 45 cm (or lengths of 25, 30, 35, 40, 50, 55, or 60 cm, for example but not by way of limitation). The occlusion balloon 214 may be 10 mm in length (or lengths of 5, 15, 20, and 25 mm in length) and inflate up to 10 mm in diameter (or up to 6, 8, 12, 14, 16, 18, or 20 mm in diameter). The guide catheter 212 may, in one non-limiting embodiment, be made from a PELLETHANE™ (Lubrizol Corporation, Wickliffe, Ohio) extrusion over stainless steel braid, an inflation lumen, and a polytetrafluoroethylene liner. The guide catheter 212 may have an outer diameter of 0.130" (or a diameter selected from 0.10, 0.11, 0.12, 0.14, and 0.15 inches) and an inner diameter of 0.101" (or a diameter selected from 0.09, 0.10, 0.11, 0.12, 0.13, and 0.14 inches).

The occluding balloon 214 may, in one non-limiting embodiment, be a polyurethane material that is thermally bonded to the guide catheter 212 and centered about a marker band on the distal end of the guide catheter 212. The proximal end of the occluding balloon 214 may have an adhesively bonded Y-connector as a hub. An upper portion of the Y-connector may have access to an inflation port and may inflate the occlusion balloon 214. Connected to a lower portion of the Y-connector may be a hemostasis valve with an extension line to allow aspiration through the sheath.

When sold and distributed, the compression system 202, capture system 204, and outer catheter system 206 may be assembled or disassembled in the form of a kit. For example, a manufacturer may position catheter shaft 208 axially within capture sleeve 210, which may in turn be positioned axially inside the guide catheter 212. Such an assembly may be delivered to a physician. Alternatively, the compression system 202, capture system 204, and/or the outer catheter system 206 may each be separately placed by the manufacturer in a single package, though separate from each other (or with any two together in the package and the other separate), or in multiple packages, and the physician can deploy them individually and then combine them—e.g., first inserting only the outer catheter system 206 into the patient, and then guiding the compression system 202 and the capture system 204, individually or together, inside and through the outer catheter system 206 previously deployed within the patient. Such a kit may also include a guide wire in alternative embodiments.

Figure 2B:
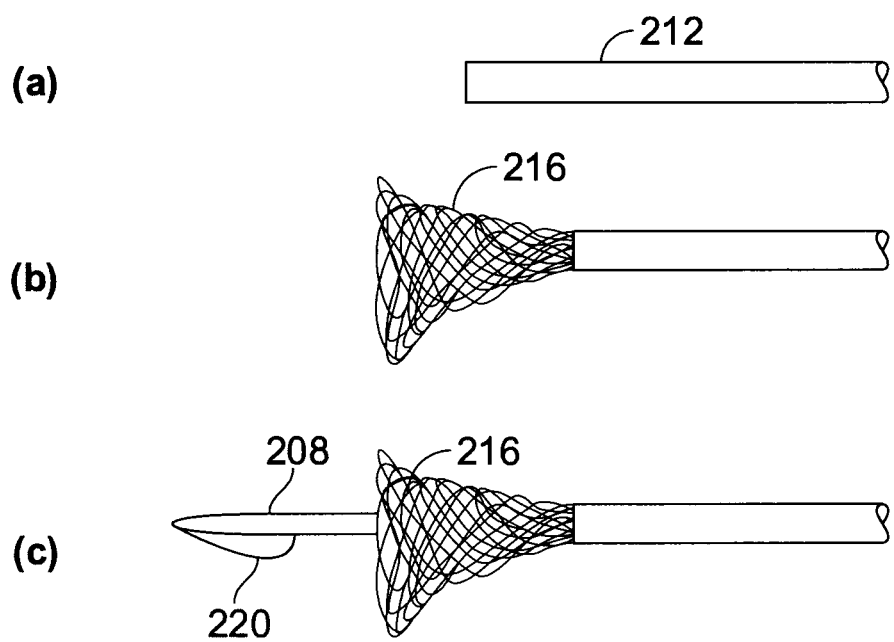
FIG. 2B is a partial nested side perspective view of the components of the peripheral embolectomy system of FIG. 2A.

FIG. 2B shows components of the peripheral embolectomy system 200 in a nested embodiment of deployment with each component being extended to differing positions with respect to one another. The components are those shown in FIG. 2A and the presentation in FIG. 2B illustrates a non-limiting embodiment of how the peripheral embolectomy system 200 can be deployed inside a patient over time by a physician, with the components being assembled into a single system.

In phase (a), the guide catheter 212 is in the captured position where the expanding funnel 216 and the capture sleeve 210 (shown in broken line format behind the distal surface of the expanding funnel 216 in FIG. 2A(a)) are both nested within both the guide catheter 212. Also, the compression device 220 is attached to the shaft 211 which is also nested within the guide catheter 212 or has not yet been inserted through the guide catheter 212 and into the patient.

At phase (b), the expanding funnel 216 has been extended distally from the distal end of the capture sleeve 210 which extends distally from the guide catheter 212 of the outer catheter system 206. As shown in phase (b), the expanding funnel 216 has been expanded radially outward such that it would be capable of engaging with the inner surface of the vessel. Before such an expansion has occurred, however, a balloon (such as occlusion balloon 214, not shown here) on a proximal end of the outer catheter system 206 may be inflated and expanded outward so as to anchor the shaft within the vasculature. Also, the capture sleeve 210 may have been extended into position beyond the end of the guide catheter 212, with the expanding funnel 216 inside, or the capture sleeve 210 may have been extended into position, and then the expanding funnel 216 extended into and through the capture sleeve 210, and out the distal end of the capture sleeve 210 into the configuration shown in phase (b).

At phase (c), the compression device 220 on the catheter shaft 208 has been extended from the distal end of the expanding funnel 216. As discussed in more detail below, the compression device 220 may be initially exposed on a proximal side of a blockage. The compression device 220 may then be extended past the blockage and expanded. While still in its expanded state (e.g., inflated), the compression device 220 is pulled back toward the distal end of the expanding funnel 216 and thereby pushes the blockage radially outward to open the vasculature and/or potentially dislodging at least a portion of the blockage and thereby enabling removal of the dislodged parts of the blockage from the vasculature. Such motion may also dislodge debris from the vascular wall and movement of the compression device 220 proximally may draw the debris back toward the distal end of expanding funnel 216. The compression device 220 may be drawn all the way proximally until it almost contacts the expanding funnel 216 or does contact actually contact and/or nest within the expanding funnel 216. The expanding funnel 216 may thereafter be withdrawn proximally and nested back into capture sleeve 210. During at least some parts of such process in one non-limiting embodiment, suction may be maintained through at least the capture sleeve 210 via a suction device associated with the capture sleeve 210 and outside the patent. Any debris and/or liquid may, in such a manner, be drawn out of the patient 100 via suction and disposed.

FIG. 2C shows the peripheral embolectomy system 200 in partial side cross-section. In general, the figure shows the same components as FIGS. 2A and 2B in a semi-nested configuration as indicated in FIG. 2C via a cross-sectional view to better show positional arrangement of the components of the peripheral embolectomy system 200.

Referring now to particular components in FIG. 2C, the guide catheter 212 of the outer catheter system 206 is shown surrounding all other components of the peripheral embolectomy system 200. An inner lumen 230 defined by an inner surface of the guide catheter 212 contains the components and, although not shown, an additional lumen may be provided on and/or within the guide catheter 212 for the inflation of a balloon (such as occlusion balloon 214). The inner lumen 230 circumscribes the guide catheter 212 (see FIG. 2D(b)). Inside the guide catheter 212 is the capture sleeve 210, which has the expanding funnel 216 mounted on and extending distally from its shaft 211. An inner surface of the shaft 211 defines a lumen space 232 in which the catheter shaft 208 is disposed. The distal end of the catheter shaft 208 may have the compression device 220 associated therewith, adhered to, or otherwise connected to the catheter shaft 208. A lumen 234 may connect to an inner part of the compression device 220 so that air or other liquid delivered through the lumen 234 may expand the compression device 220 outward. Where there are more than one compression device 220 at the end of or along the longitudinal length of the catheter shaft 208, a single lumen (such as the lumen 234) can lead to all and they may be inflated together (though some may delay their inflation by being made of a material that requires higher internal pressure before it will stretch outward radially, as compared to other of the compression devices), or multiple lumens may exist so that particular compression devices can be inflated separately from other compression devices.

Each of the concentrically-located subsystems 202, 204, 206 may be movable longitudinally relative to each of the other subsystems. For example, the compression device 220 may be moved distally and proximally without moving the shaft 211, the guide catheter 212, or the capture sleeve 210. Alternatively, the sleeve 210 and associated expanding funnel 216 may be moved longitudinally either distally or proximally without moving the guide catheter 212 or the catheter shaft 208. Also, shaft 211 and expanding funnel 216 can be slid longitudinally inside capture sleeve 210.

FIGS. 2D(a) and 2D(b) show cross-sectional transverse views of the configuration of the peripheral embolectomy system 200 illustrated in FIG. 2C. FIG. 2D(a) provides a view of the peripheral embolectomy system 200 looking back at the peripheral embolectomy system 200 from a position beyond its distal end. The mesh of the expanding funnel 216 (in its expanded form) can be seen in this view. The capture sleeve 210 and the guide catheter 212 are also visible behind the expanding funnel 216 in its expanded configuration. Inside the expanding funnel 216, the catheter shaft 208 and compression device 220 can be seen, which highlights how the compression device 220 can be extended longitudinally distally from the expanding funnel 216 to interact with blocking material in the vasculature. Dislodged material can be captured by the expanding funnel 216 and routed into the inner lumen 232 for aspiration out of the patient 100.

FIG. 2D(b) shows a transverse cross-section of the configuration of the peripheral embolectomy system 200 of FIG. 2C at a position proximal to the view of FIG. 2D(a). The view here is shown at a location where the occlusion balloon 214 is affixed around the periphery of the guide catheter 212 in order to provide a visual example of how inflating and deflating fluids can be passed through the peripheral embolectomy system 200. In particular, a wall 246 defines a lumen 247 inside the guide catheter 212 (shown and contemplated as a braided material in FIG. 2D(b)) that is sealed from the lumen 230. The lumen 230 may be open at the distal end of the peripheral embolectomy system 200 and thus a suitable mechanism for passing inflation air or other liquids to the occlusion balloon 214. The lumen 247 defined by wall 246 may thus provide a mechanism for inflation/deflation of the occlusion balloon 214 via passage 242. In appropriate circumstances, multiple passages to the occlusion balloon 214, multiple separate occluding balloons (e.g., spaced from each other around the periphery of or spaced longitudinally from each other along the guide catheter 212), and/or multiple longitudinal inflation lumens may be provided in the system (e.g., to provide for faster and/or selective inflation of the one or more occlusion balloon(s) 214). The occlusion balloon 214 in the embodiment shown in FIG. 2D(b) is shown as being implemented via two balloons on opposed sides of the guide catheter 212, but may generally extend as a single balloon (and single lumen) around the entire periphery of the guide catheter 212.

Likewise, an inner surface of the catheter shaft 208 defines an inner lumen 234 that may inflate and deflate the compression device 220 (such as a balloon) that may communicate fluidly with the lumen 234 by being attached to an open distal end of the catheter shaft 208, or via a passage in the side of the catheter shaft 208. In this view, the expanding funnel 216 is also shown surrounding the catheter shaft 208, so that the various components define lumens 230, 232, and 234.

Figure 3A:
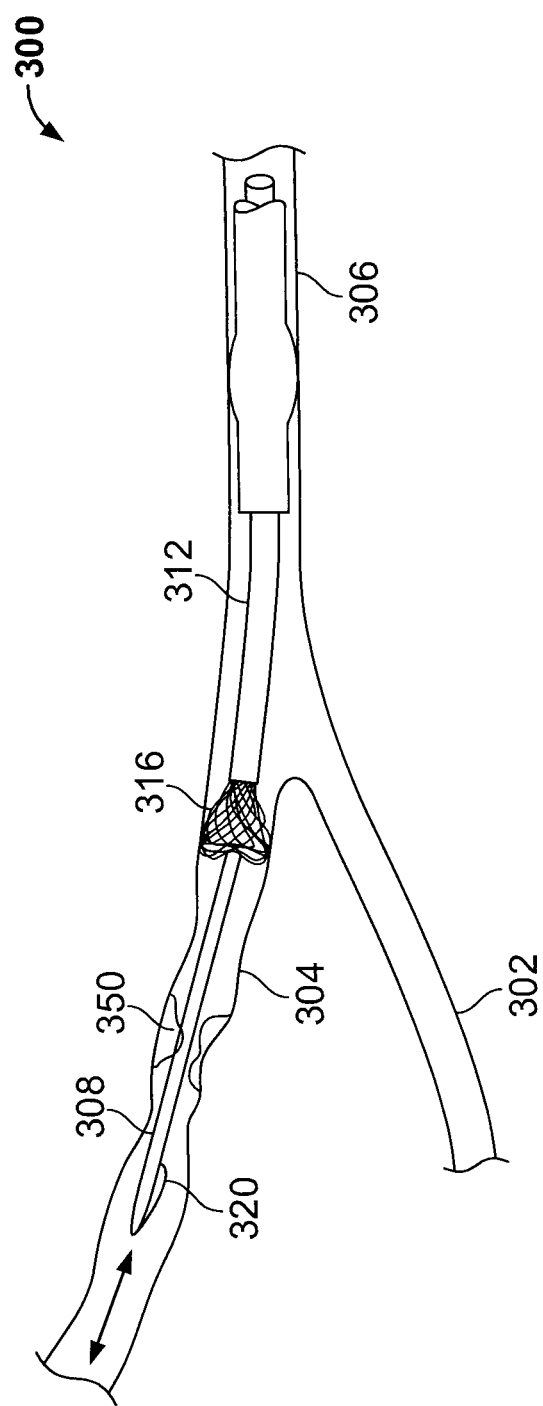
FIG. 3 shows a peripheral embolectomy system in use in a patient's vasculature.

FIG. 3A shows a peripheral embolectomy system 300 in use in a patient's vasculature. In general, peripheral embolectomy system 300 is similar to the embolectomy system 50 shown in FIG. 1 and embolectomy system 200 shown in FIGS. 2A, 2B, and 2C, except as described herein below.

In this example, there is shown a femoral artery 306 with a first branch 302 and a second branch 304. A sheath 312 of a catheter 309 has been passed down the femoral artery 306 and steered into the second branch 304. A balloon 314 on the catheter 309 has been expanded against the walls of the femoral artery 306 so as to anchor the catheter 309 in the femoral artery 306. In addition, the balloon 314 (in its expanded state) stagnates/stops blood flow through femoral artery 306 and assists in the prevention of pieces of debris that might come from a blockage from traveling downstream in the artery 306.

With the sheath 312 in place with its distal end down into the second branch 304, a mesh funnel 316 has been extended outward from the distal end of the sheath 312 and has been expanded radially such that it rests at least partially against the wall of the second branch 304. As noted above, the mesh funnel 316 may be composed of nitinol shape memory wire that may be bare or covered (e.g., a single layer of wire with a single layer of material laid on it and attached to it, or two or more layers of material wrapped around distal and proximal sides of the funnel) or filled with another material (e.g., a layer of material between two or more layers of wire) such as a PTFE cloth.

Extended out distally from the mesh funnel 316 is a shaft 308 and compression device 320 at the end of the shaft 308. The distal end of the shaft 308, and the compression device 320 thereon, have been extended distally past a blockage 350 in the second branch 304 (although shown as a partial blockage in FIG. 3A, the blockage may also be complete) while compression device 320 has remained in a non-expanded state. Once the compression device 320 is located distally from the blockage 350, as shown in FIG. 3A, the compression device 320 may be expanded, such as by a physician applying a pressurized liquid through a lumen in shaft 308, to thereby increase the pressure and inflate the compression device 320. Once inflated, the compression device 320 exerts a radial force on the walls of the vasculature—i.e., within the second branch 304 of the femoral artery 306.

Once the compression device 320 is in its expanded state, the physician may draw shaft 308 proximally so that the compression device 320 passes through the length of the blockage 350 while it remains in its expanded state. In this manner, the compression device 320 pushes the blockage 350 outward against the wall of the vessel thereby opening the diameter of the second branch 304. The proximal movement of the compression device 320, moving through the blockage 350, may also dislodge or break-up portions of the blockage 350 thereby creating debris in the blood flow inside the second branch 304. Such debris may be captured by the mesh funnel 316 and/or caught or blocked by the balloon 314. Such debris may stay on such items (i.e., the mesh funnel 316 and/or the balloon 314 may have an exterior surface coating or modification that has an affinity for sticking to or otherwise being associated with the debris) and/or be drawn into lumens inside the sheath 312 to be aspirated out of the patient 100.

As discussed above, the compression device 320 may take a variety of forms and be covered or filled with chemicals to provide beneficial effects on the walls of the vasculature. For example, when the compression device 320 is in the form of a balloon it may comprise a structure or material that is drug-eluting and/or drug coated. Such drugs may erode off and/or elute from the balloon as it is pulled proximally through the vasculature. In some embodiments, the drug may be activated after the compression device 320 is in place. As one example, the drug may be encapsulated in beads that are adhered to the surface of the compression device 320, and the beads may pop and release the drug when the compression device 320 places enough force against the vessel wall to cause the beads to fail. The drug may also be encased in a temperature-sensitive material on the outside of the compression device 320, such as a material having a melting point slightly higher than the internal temperature of a patient's body. When the compression device 320 is in place and expanded, warm fluid, such as saline, may be circulated through the inside of the compression device 320 in order to melt the encasing material (which may be a material that is biocompatible in liquid form and may thus be absorbed back into the patient's body) thereby releasing the drug into the tissue of the inner vessel wall and/or into the patient 100, generally.

Figure 3B:
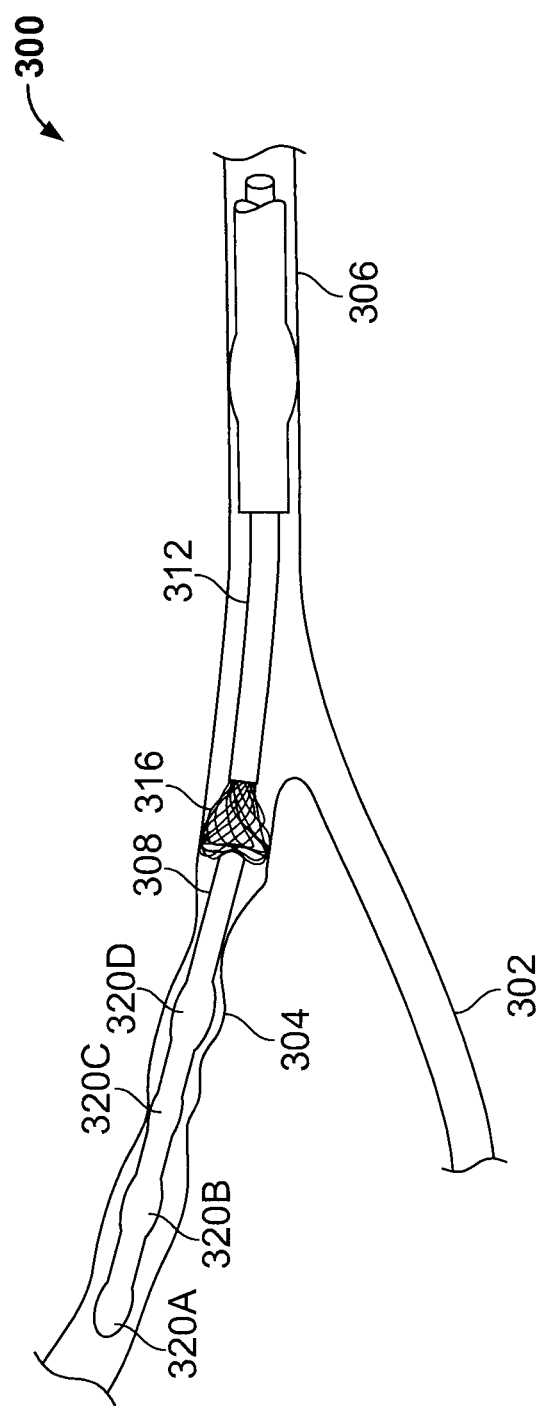

FIG. 3B shows a peripheral embolectomy system 330 in use in a patient's vasculature. In general, the system 330 is similar to system 300 in FIG. 3A, but is provided with multiple compression devices 320A-320D at its distal end.

In particular, the femoral artery 306 again houses the catheter 309 with expanded balloon 314 holding it in place. A sheath 312 extends form the distal end of the catheter 309 and into the second branch 304 of the vasculature. The catheter 309 and sheath 312 may have been extended distally while a physician monitored their progress using standard imaging techniques along with markers as discussed above for FIG. 1. The shaft 308 extends distally from the mesh funnel 316. The mesh funnel 316 extends distally from the sheath 312 and has been expanded so as to contact a vessel wall around essentially the entire periphery of the mesh funnel 316.

In this example, a plurality of compression devices 320A-320D are arranged along a terminal portion of an outer surface of the shaft 308. At the time of this figure, compression device 320D is in its expanded state and the remaining compression devices 320A-320C are in their collapsed state. The compression device 320D may be in the process of being pulled proximally past and over a particularly narrow blockage in the vessel. As the compression device 320D passes the blockage, a physician may cause it to be collapsed, and compression device 320C to be expanded and then pulled across and through the blockage. The process may be repeated as the shaft 308 continues to be pulled proximally and compression devices 320B and 320A, in turn, are expanded and then contracted.

In another embodiment, each of compression devices 320A-320D may be expanded simultaneously with each other, but may expand to different radial sizes. For example, compression device 320D may be the smallest, and each successive device may be slightly larger than the prior compression device. In this manner, if the blockage is very narrow, the compression device 320D may first pass through it and open it slightly, compression device 320C may be slightly larger and open the blocked area up a bit more, compression device 320B may open the blocked area a bit more, and compression device 320A may open the blocked area a final amount. In this manner, the opening of the blockage may be made in progressive steps of increasing size rather than a single compression device 320. In a similar manner, a single compression device 320 may be employed, and may be extended distally past a blockage, expanded, and then drawn proximal to the blockage, with the process repeating while the compression device is radially expanded an additional amount for successive cycles, so as to gradually dilate the vessel further and further.

Figure 4:
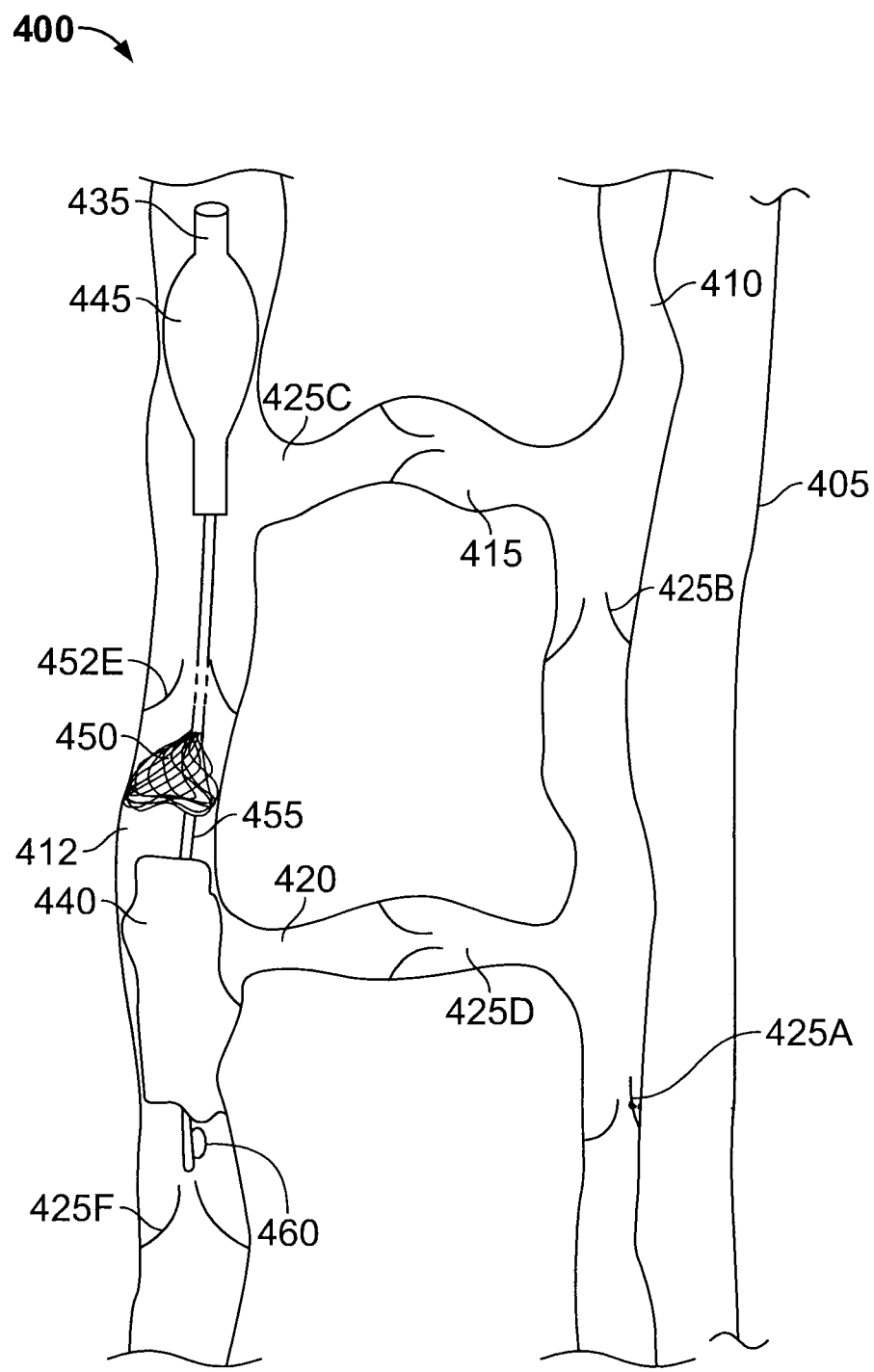
FIG. 4 shows a venous embolectomy system in use in a patient's vasculature.

FIG. 4 shows a venous embolectomy system 400 in use in a patient's venous vasculature. In general, the venous embolectomy system 400 is similar to the embolectomy system 50 shown in FIG. 1 and the peripheral embolectomy system 200 shown in FIGS. 2A, 2B, and 2C, except that the venous embolectomy system 400 has been adapted for use in venous vasculature.

In this embodiment, there is shown an illustration of a patient's leg and venous vasculature therein. More particularly, there is shown the outer skin 405 of a patient and a superficial vein 410, a deep vein 412, a first perforating vein 415, a second perforating vein 420, and a plurality of venous valves denoted as 425A-F. A sheath 430 of a catheter 435 has been passed down the deep vein 410 and steered into a position proximal a blockage 440. A balloon 445 on the catheter 435 has been expanded against the walls of deep vein 410 so as to anchor the catheter 435 in the deep vein 410. In addition, the balloon 445 in its expanded state stagnates/stops blood flow through the deep vein 410 and assists in the prevention of pieces of blockage debris from traveling upstream in the deep vein 410. Although the catheter 435 is shown in FIG. 4 as being passed down the deep vein 410, it is also contemplated that the catheter 435 may be inserted into the superficial vein 410 and steered through one of the first and second perforating veins 415, 420 into the deep vein 410 proximal the blockage 440. In the event that a blockage exists primarily or secondarily in the superficial vein 410 or in one or more of the first and second perforating veins 415, 420, the catheter 435 may be inserted into the deep vein 410 and steered through the venous vasculature such that the catheter 435 is in a proximal position with respect to such a blockage.

With the sheath 430 in place with its distal end proximal the blockage 440, a mesh funnel 450 has been extended outward from the distal end of the sheath 430 and has been expanded against the wall of the deep vein 410. As noted above, the mesh funnel 450 may be composed of nitinol shape memory wire that may be bare or covered (e.g., a single layer of wire with a single layer of material laid on it and attached to it, or two or more layers of material wrapped around distal and proximal sides of the mesh funnel 450) or filled with another material (e.g., a layer of material between two or more layers of wire), such as a PTFE cloth.

Extended out distally from the mesh funnel 450 is a shaft 455 and compression device 460 at the end of the shaft 455. The distal end of the shaft 455, and the compression device 460 thereon, has been extended distally past the blockage 440 in the deep vein 410 (although shown as a complete blockage in FIG. 4, the blockage may also be an incomplete blockage) while compression device 460 has remained in a non-expanded state. Once the compression device 460 is located distally from the blockage 440, as shown in FIG. 4, the compression device 460 may be expanded, such as by a physician applying a pressurized liquid through a lumen in shaft 455, to thereby increase the pressure inside and thereby inflate the compression device 460. Once inflated, the compression device 460 exerts a radial force on the walls of the vasculature—i.e., deep vein 410.

Once the compression device 460 is in its expanded state, the physician may draw the shaft 455 proximally so that the compression device 460 passes through the length of the blockage 440 while it remains in its expanded state, thereby pushing the blockage 440 radially outward against the wall of the vessel and opening the diameter of the deep vein 410. The proximal movement of the compression device 460 moving through the blockage 440 may also potentially dislodge or break-up portions of the blockage 440 thereby creating debris in the blood flow inside the deep vein 410. Such debris may be captured by the mesh funnel 450 and/or caught or blocked by the balloon 445 and may stay on such items, and/or be drawn into lumens inside of the sheath 430 to be aspirated out of the patient 100.

It is contemplated that in at least one embodiment, the balloon 445 and/or the compression device 460 may be composed of a material and/or be coated with a material that lends a tackiness to their surfaces. Such tackiness provides a mechanism by which debris released by the blockage 440 may be immobilized to the venous embolectomy system 400 and withdrawn from the vasculature. In one embodiment, an outer surface of the balloon 445 has been modified (for example, but not by way of limitation, via dipping, coating, spraying or otherwise treating) to increase the friction existing between the outer surface of the balloon 445 and the inner vessel wall. Such a higher friction surface supports or enables better emboli removal from the vessel walls and venous valves. Such tacky or high friction coatings are well known to those of skill in the art and are to be considered as part of the presently disclosed and/or claimed inventive concept(s). For example, but not by way of limitation, such tacky or high friction coatings are manufactured by Vention Medical of South Plainfield, N.J.

As discussed above with respect to the compression device 320, the compression device 460 may take a variety of forms and be covered or filled with chemicals to provide beneficial effects on the walls of the vasculature. For example, when the compression device 460 is in the form of a balloon it may comprise a structure or material that is drug-eluting and/or drug-coated. Such drugs may erode off and/or elute from the balloon as it is pulled proximally through the vasculature. The disclosure hereinabove with respect to the compression device 320 is equally applicable and can be applied to the compression device 460. Furthermore, as discussed with respect to the shaft 308, the shaft 455 may comprise a plurality of compression devices similar to compression devices 320A-320D. The disclosure hereinabove with respect to compression devices 320A-320D is equally applicable and can be applied to a plurality of compression devices being associated with the shaft 455.

As shown in FIG. 4, the venous vasculature also comprises a plurality of venous valves, such as the venous valves denoted as 425A-F. These venous valves are bicuspid (two) flap like structures made of elastic tissue. Blood flow in the major veins of the lower extremity depends, in part, on the pumping action produced by leg muscle contractions. Retrograde blood flow is prevented by the venous valves. Chronic venous insufficiency (CVI) is a condition that occurs when the venous wall and/or valves in the leg veins are not working effectively, making it difficult for blood to return to the heart from the legs. CVI causes blood to "pool" or collect in these veins often leading to partial and/or complete blockages resulting from clots or other types of emboli as well as enlarged veins and deformed valves. These emboli are life-threatening if they migrate to lungs, for example.

The venous embolectomy system 400 is especially well suited to the treatment of deep vein thrombosis (DVT). In one embodiment where the compression device 460 has a tacky surface, pulling the compression device 460 through one of the venous valves (e.g., venous valve 425E) allows the compression device to dislodge clots or other DVT debris from the venous valves. In effect, pulling the compression device 460 through one of the venous valves allows clot material to be pulled off of the valve. Once cleaned in this manner, the function of the venous valve is improved and blood flow through the venous valve is restored.

In particular embodiments, the venous embolectomy system 400 is sized and shaped similarly to the embolectomy system 50 (FIG. 1) and/or the peripheral embolectomy systems 200, 300 (FIGS. 2-3). In one embodiment, the components of the venous embolectomy system 400 are sized and shaped to conform to the sizes and shapes of the venous vasculature. For example but not by way of limitation, the sheath 430 is from about 9 to about 10 French, the mesh funnel 450 is able to expand to a diameter greater than or equal to 14 mm, and the compression device 460 is able to expand to a diameter of at least 14 mm. In another embodiment, the sheath 430 is of a size from about 9 to about 12 French, the mesh funnel 450 is able to expand to a diameter from about 8 mm to about 18 mm, and the compression device 460 is able to expand to a diameter from about 10 mm to about 18 mm.

Figure 5:
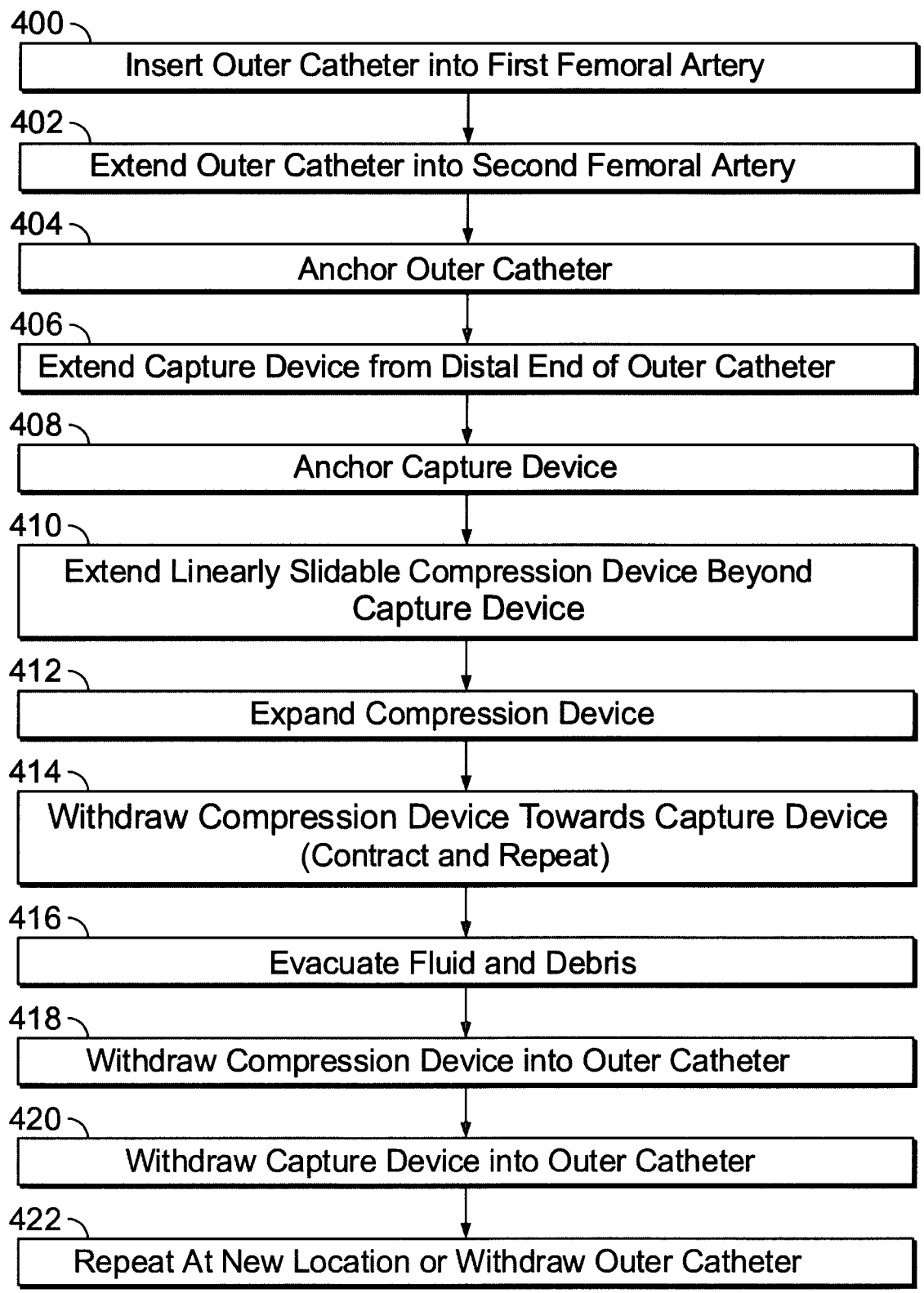
FIG. 5 is a flow chart of a method for performing peripheral embolectomy.

FIG. 5 is a flow chart of a method for performing an embolectomy and, more particularly, a peripheral embolectomy. In general, the method may be performed using the structures pictured and described with respect above, and similar structures. Also, the structures above have been described with particular processes, and actions from those processes may be combined as appropriate with the actions described for the method here.

The process begins at box 400, where an outer catheter is inserted into a first femoral artery. In such a step, a physician in an appropriately outfitted procedure room may make a small incision in a conventional manner in an inner thigh of a patient and move the catheter into the artery. At box 402, the outer catheter is extended into a second femoral artery location. For example, the physician may advance the catheter through the incision, pushing it into the patient, and may steer the catheter across to the second femoral artery.

At box 404, the outer catheter may be anchored within the patient. For example, a band on the catheter may be viewed by way of imaging techniques such as fluoroscopy, and the physician may stop advancing the catheter when the band reaches a determined distance from a blockage that is to be addressed by the procedure. For example, the physician may determine to anchor the catheter when a band that surrounds a balloon on the catheter is one or two inches away from a proximal end of the blockage. The particular distance will vary based on the construction of the catheter, such as the distance from a balloon on the catheter and the distal end of the catheter, and also on the particular patient, such as the distance from a blockage to a branch in the vasculature of the patient. The anchoring of the capture device may occur, for example, by the physician applying an inflating fluid to inflate a balloon that surrounds the outer catheter, so that the balloon fits tightly within the vasculature.

At box 406, a capture device is extended from a distal end of the outer catheter. For example, a nitinol wire funnel may be inserted into a proximal end of the catheter by the physician and advanced down the catheter to the distal end of the catheter. The physician may use imaging techniques to observe the relative position of the capture device and may continue advancing until it is extended out of the end of the outer catheter, and is seen to be extended far enough to expand against the walls of the vasculature. At box 408, the physician may anchor the capture device, such as by locking it in place at a proximal end of the outer catheter or simply by the capture device contacting the vasculature so that it stops moving longitudinally relative to the system.

At box 410, the physician extends a linearly slidable compression device beyond the capture device. Such compression device may, for example, constitute a shaft having an inner lumen and an expandable balloon attached to the end of the shaft and in fluid communication with the lumen. The extension of the compression device may also be tracked by imaging, such as by a band that is placed on the shaft or on the balloon, and the physician may extend the compression device so that it moves from a proximal end of a blockage, into the blockage, and potentially past a distal end of the blockage.

At box 412, the compression device is expanded so that the device moves closer to the wall of the vasculature and/or contacts the wall. The extent to which the compression device is expanded may vary, and may generally be selected to be an amount so that the compression device is wider than a passage through the blockage, but is not so wide as to prevent passage of the expanded compression device longitudinally through the blockage.

At box 414, the physician withdraws the compression device toward the capture device. For example, the physician may pull on a proximal end of the shaft for the compression device manually by hand, or by use of a mechanical structure, such as a motor in the form of a stepper motor that may be used to control the amount of force applied to the shaft Such withdrawing of the compression device may cause the compression device to push against the material that forms the blockage, thus pushing such material outward and enlarging the passage of the blockage, and also potentially dislodging portions of the material in creating debris inside the vasculature. Such debris may be pulled back by the compression device toward the capture device and then aspirated with the capture device into a lumen of the outer catheter and potentially outside the patient.

Such motion of the compression device relative to the blocking material may be repeated multiple times as needed. For example, a physician may repeatedly pass the compression device to a distal end of the blockage, inflate the compression device, draw the compression device back through the blockage in a proximal direction, deflate the compression device, and move the compression device back to the distal end of the blockage again. Such steps may be repeated by the physician until, in the physician's medical judgment; adequate effect on the blockage has been achieved.

In the process, the physician may also perform additional steps, including by introducing a stent or other device at or around a blockage, by introducing one or more runs in or around a blockage such as drugs to prevent the regrowth of tissue in the blockage and other similar steps.

Moreover, drugs (e.g., anti-clotting or anti-restenosis drugs) may be administered through the compression device or from the outer surface of the compression device, in various manners like those discussed above.

At box 416, fluid and debris from the area of the procedure may be evacuated out of the patient. For example, aspiration device connected to a Y-connector may pull fluid and debris into a container or other disposable mechanism that may be removed from the site of the procedure.

At box 418, the compression device may be withdrawn into the outer catheter after being moved to a non-expanded state, and may also be withdrawn out of the patient, such as by the physician manually pulling on the shaft that supports the compression device. At box 420, the capture device may be withdrawn into the outer catheter, such as by the physician pulling manually on a sleeve to which the capture device is connected. And at box 422, the procedure may be repeated at a new location on a different blockage, or the outer catheter may be withdrawn from the patient in a conventional manner and the procedure ended.

The combinations of any of the method steps described herein above may be performed simultaneously or wholly or partially sequentially. In addition, the exemplary sequences of method steps provided herein above are for the purposes of illustration only; it will be understood that the individual steps, as well as the particular order of steps, may vary, and the sequence of steps may be performed in any order, so long as the materials and packages described herein are capable of functioning in accordance with the presently disclosed inventive concept(s).

Thus, in accordance with the presently disclosed inventive concept(s), there has been provided embolectomy systems and methods, packaged products and kits formed therefrom, as well as methods of producing and using same that fully satisfy the objectives and advantages set forth herein above. Although the presently disclosed inventive concept(s) has been described in conjunction with the specific language set forth herein above, it is evident that many alternatives, modifications, and variations will be apparent to those skilled in the art. Accordingly, it is intended to embrace all such alternatives, modifications, and variations that fall within the spirit and broad scope of the presently disclosed inventive concept(s). Changes may be made in the construction and the operation of the various components, elements, and assemblies described herein, as well as in the steps or the sequence of steps of the methods described herein, without departing from the spirit and scope of the presently disclosed inventive concept(s).

What is claimed is:

1. An endovascular apparatus for introduction into a blood vessel, comprising:
   an outer guide catheter having a first proximal end, a first distal end, a first outer surface, and a first inner surface, the first inner surface of the outer guide catheter defining a first cannula extending along a first longitudinal length from the first proximal end to the first distal end of the outer guide catheter, the outer guide catheter having an outer periphery and an expandable portion radially disposed about at least a portion of the outer periphery,
      wherein when the outer guide catheter is in a deployed state, the first outer surface adjacent to the expandable portion is configured to abut an inner surface of a first portion of the blood vessel to thereby occlude the blood vessel;
   a capture sleeve having a second proximal end, a second distal end, a second outer surface, and a second inner surface, the second inner surface defining a second cannula having a first diameter extending along a second longitudinal length from the second proximal end to the second distal end of the capture sleeve, the capture sleeve configured to be disposed within the first cannula of the outer guide catheter such that at least a portion of the second outer surface of the capture sleeve is adjacent the first inner surface of the outer guide catheter, the capture sleeve having freedom of movement along the first longitudinal length of the outer guide catheter;
   a shaft having a third proximal end, a third distal end, a third outer surface, and a third inner surface, the third inner surface defining a third cannula having a second diameter extending along a third longitudinal length from the third proximal end to the third distal end of the shaft, the shaft having an expandable capture device positioned adjacent to the third distal end of the shaft, the shaft and the expandable capture device are configured to be disposed within the second cannula of the capture sleeve such that the second diameter of the third cannula of the shaft is less than the first diameter of the second cannula of the capture sleeve, the shaft and the expandable capture device having freedom of movement along the second longitudinal length of the capture sleeve,
      wherein when the shaft and the expandable capture device are in a deployed state, at least a portion of the expandable capture device extends out of the second cannula of the capture sleeve and expands radially outward to form a radially expanded configuration, and the third outer surface of the shaft is spaced a distance away from the second inner surface of the capture sleeve to provide an inner lumen therebetween, and
      wherein in the radially expanded configuration at least an outer portion of the expandable capture device is configured to abut the inner surface of a second portion of the blood vessel that is located a first distal distance from the first portion of the blood vessel; and
   a catheter shaft having, a fourth proximal end, a fourth distal end, a fourth outer surface, and a fourth inner surface, the fourth inner surface defining a lumen having a third diameter extending along a fourth longitudinal length from the fourth proximal end to the fourth distal end of the catheter shaft, a distal end of the lumen being in fluid communication with a compression member disposed at a terminal point of the fourth distal end of the catheter shaft, the catheter shaft is configured to be disposed within the third cannula of the shaft such that the third diameter of the lumen of the catheter shaft is less than the second diameter of the third cannula of the shaft such that the fourth outer surface of the catheter shaft is spaced a distance away from the third inner surface of the shaft to provide an inner space therebetween, the catheter shaft having freedom of movement along the third longitudinal length of the shaft,
      wherein when the compression member is in a deployed state the fourth distal end of the catheter shaft having the compression member disposed thereat extends beyond the third distal end a fifth longitudinal length and an outer surface of the compression member is configured to abut the inner surface at a third portion of the blood vessel that is located a second distal distance from the second portion of the blood vessel and distal to a blockage in the blood vessel.

2. The endovascular apparatus of claim 1, wherein the compression member comprises a drug-coated or a drug-eluting balloon.

3. The endovascular apparatus of claim 1, wherein the expandable capture device comprises a shape memory wire mesh sized and shaped to expand radially outward from a longitudinal plane extending through the center of the third cannula.

4. The endovascular apparatus of claim 3, wherein the expandable capture device further comprises a film or fabric covering at least a portion of the shape memory wire mesh.

5. The endovascular apparatus of claim 1, wherein the catheter shaft further includes at least one expandable balloon disposed around the catheter shaft proximal to the compression member, wherein when the compression member and the at least one expandable balloon are in a deployed state, an outer surface of the expandable balloon and the outer surface of the compression member are configured to abut the inner surface of the third portion of the blood vessel.

6. The endovascular apparatus of claim 5, wherein the at least one expandable balloon and the compression member are configured to be placed distally to the blockage in the blood vessel and a second expandable balloon is located proximal to the blockage in the blood vessel.

7. The endovascular apparatus of claim 1, wherein the compression member has a cross-sectional diameter of from about 4 mm to about 10 mm.

8. The endovascular apparatus of claim 1 in the form of a kit for performing endovascular surgery wherein at least two of the outer guide catheter; the capture sleeve, the shaft, and the catheter shaft are located separate from one another.

9. The endovascular apparatus of claim 1 in the form of a kit for performing endovascular surgery wherein the outer guide catheter, the capture sleeve, the shaft, and the catheter shaft are located separate from one another.

* * * * *